(12) United States Patent
Meier et al.

(10) Patent No.: US 6,592,735 B1
(45) Date of Patent: Jul. 15, 2003

(54) DNA SEQUENCING MACHINE WITH IMPROVED COOLING CHARACTERISTICS

(75) Inventors: Joseph T. Meier, So. Pasadena, CA (US); Steven M. Clark, Palo Alto, CA (US); Charles F. Spence, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 121 days.

(21) Appl. No.: 09/746,339

(22) Filed: Dec. 22, 2000

Related U.S. Application Data
(60) Provisional application No. 60/184,694, filed on Feb. 24, 2000, and provisional application No. 60/171,847, filed on Dec. 22, 1999.

(51) Int. Cl.[7] .............................................. G01N 27/26
(52) U.S. Cl. ...................... 204/621; 204/616; 204/617; 204/618
(58) Field of Search ................................ 204/616, 618, 204/621, 466, 467, 617

(56) References Cited

U.S. PATENT DOCUMENTS

| | | | | |
|---|---|---|---|---|
| 3,932,263 A | * | 1/1976 | Brefka | 204/617 |
| 5,746,901 A | * | 5/1998 | Balch et al. | 204/456 |
| 5,888,364 A | * | 3/1999 | Schuette | 204/466 |
| 6,236,945 B1 | * | 5/2001 | Simpson et al. | 435/6 |

FOREIGN PATENT DOCUMENTS

| | | | |
|---|---|---|---|
| EP | 0268406 A2 | * | 5/1986 |
| JP | 02-143145 | * | 6/1990 |
| JP | 05-249078 | * | 9/1993 |

OTHER PUBLICATIONS

Polyethylene, High density entry in "Polymers—A Property Database", Chapman & Hall/CRC Press 2000, downloaded from www.knovel.com.*
LDPE entry in "Polymers—A Property Database", Chapman & Hall/CRC Press 2000, downloaded from www.knovel.com.*
Thermal Conductivity of Glass table, CRC Handbook of Chemistry and Physics (3rd electronic edition) CRC Press 2000, downloaded from www.knovel.com.*
JPO computer translation of Hajime et al. (JP 05–249078).*
JPO abstract of Taira et al. (JP 402143145 A).*

* cited by examiner

Primary Examiner—Nam Nguyen
Assistant Examiner—Alex Noguerola
(74) Attorney, Agent, or Firm—Fish & Richardson P.C.

(57) ABSTRACT

A machine for sequencing DNA using optical techniques. A sample is loaded in the sample loading area, and place through DNA sequencing gel. The voltage across the reservoir may be increased by improving the cooling and thermal characteristics of the gel device. Preferably materials are used which have at least half and preferably a fifth the thermal transfer characteristics of glass. The materials can also be thin e.g. 50–100 microns. A heat sink can be used to dissipate more of the heat, and a fan can be directed at the heat sink. Moreover, the material can be flexible.

18 Claims, 5 Drawing Sheets

DNA SEQUENCING MACHINE WITH IMPROVED COOLING CHARACTERISTICS

This application claims priority from Provisional application No. 60/171,847, filed Dec. 22, 1999, and from application No. 60/184,694, filed Feb. 24, 2000.

BACKGROUND

DNA sequencing can be carried out to find the contents of a DNA molecule. Sequencing of this type may be done by using a slab gel to separate DNA molecules. The gel is heated to denature the DNA molecules, and then acts like a sieve so that different molecular parts travel at different speeds.

The rate of migration of DNA molecules that are 1 kb or smaller through a gel is approximately related to a linear function of the voltage across the gel. Therefore, it may be desirable to apply a higher voltage gradient across these gels, to increase the speed of the process.

SUMMARY

It has been found by the present inventors that the gel plus buffer combination may behave as a bulk resistive material. As larger voltages are applied across the gel, more power is dissipated due to Joule heating.

The inventors found that this heat should be removed to prevent the matrix temperature from rising to a point where melting or bubble formation occurs. These latter effects could effect or destroy the separation properties of the matrix. It has been found that energy dissipation efficiency of the matrix may be a primary limiting factor in the voltage gradient they can be applied to a gel, e.g. and acrylamide gel or more generally any separation matrix.

In addition, a temperature gradient caused by cooling which is too intense may actually effect the measurement. The present application also describes minimizing temperature gradients during the voltage application.

The present application describes a system which allows the significant heat dissipation, retaining the advantages of slab gels, but allowing heat to be dissipated therefrom.

In one embodiment, a thin support structure is used which removes energy generated by Joule heating of the gel. This is done without generating a large temperature differential across the support medium.

BRIEF DESCRIPTION OF THE DRAWINGS

These and other aspects will now be described in detail with reference to the accompanying drawings, wherein.

DETAILED DESCRIPTION

Figure 1:
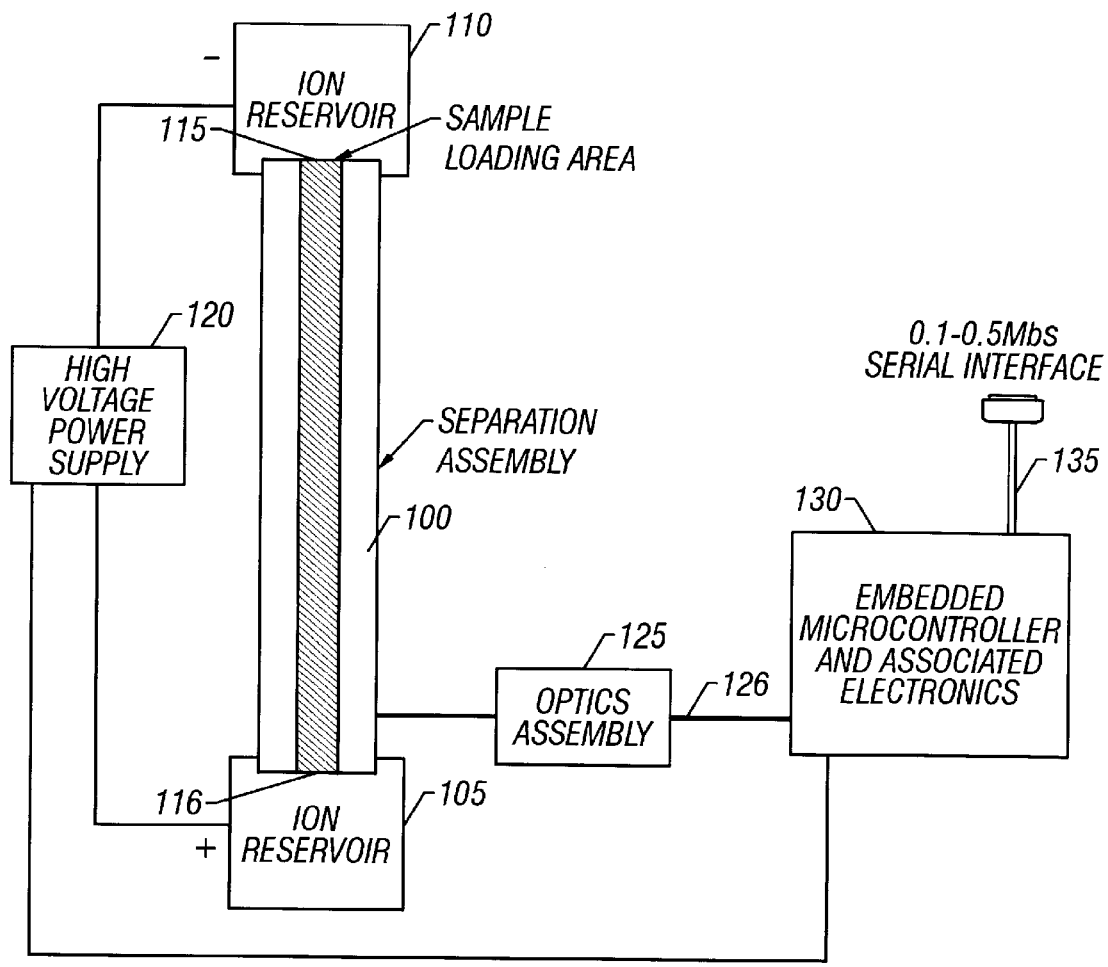
FIG. 1 shows a block diagram of the DNA sequencing instrument in a linear configuration.

A block diagram of a first embodiment of the apparatus is shown in FIG. 1. A separation assembly 100 is located between two ion reservoirs 105, 110. The ion reservoirs can be buffer boxes for example. The sample is loaded at a sample loading area 115 which is adjacent one end of the device. The separation assembly extends from that end to another end at 116 adjacent the other ion reservoir. A high voltage power supply 120 is connected for excitation of the gel as conventional. The high voltage power supply can use a flyback transformer with a voltage multiplier and filter circuit. This power supply architecture can be similar to that used in television picture tubes in order to use more conventional parts and thereby reduce the cost. The power supply can also generate electric fields for electrodes for reasons as described herein.

An optics assembly 125 detects the fluorescence of the labeled DNA fragments as they are produced. The output of the optics assembly 126 is coupled to a processor which controls the instruments and acquires the data. The microprocessor can have an I/O device 135 which communicates data to and from the processor.

The inventors noticed that temperature differential in such a system is dependent on thickness of the support material and its thermal conductivity. The materials described herein use thermal conductivities which are less than those of glass, i.e. are one half to one half of a similar device made of glass. A thin support structure also helps with the heat dissipation problem. The support can be, for example, 50–100 microns thick.

This thin support structure has a decreased cross-sectional area and decreased applied power. Since there is less of the gel, less heat is captured, allowing faster operation. It is also desirable to establish temperature equilibrium. The low mass system of the present application can allow equilibrium to be established more quickly. In one embodiment, a elongated heater layer 207 to be included into the aluminum heat sink. The heater can be resistively heated to facilitate bringing the assembly to its specified temperature, e.g. the equilibrium temperature.

Figure 2:
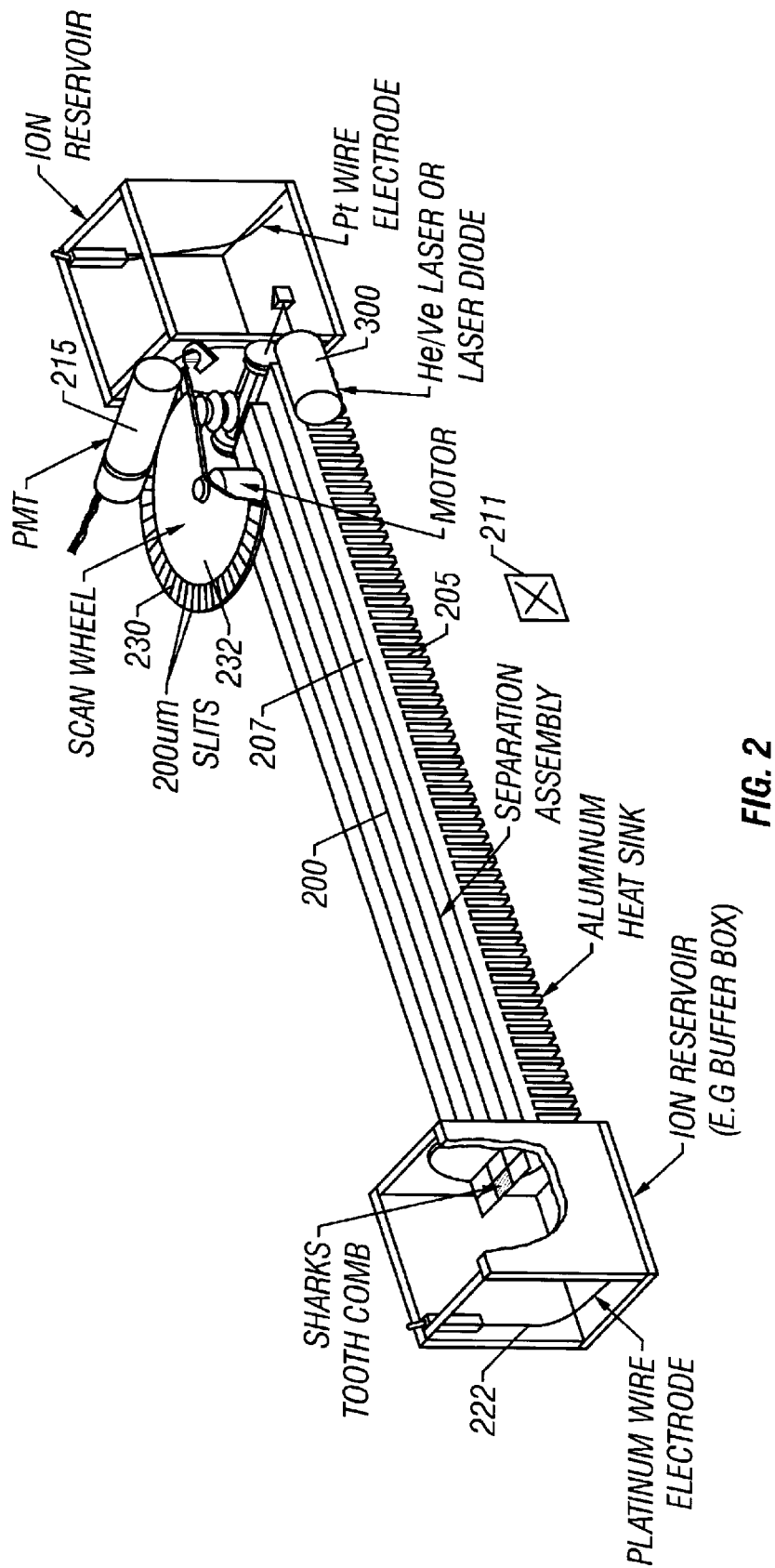
FIG. 2 shows further detail of the linear configuration including the heat sink and the scanning wheel.
Figure 3:
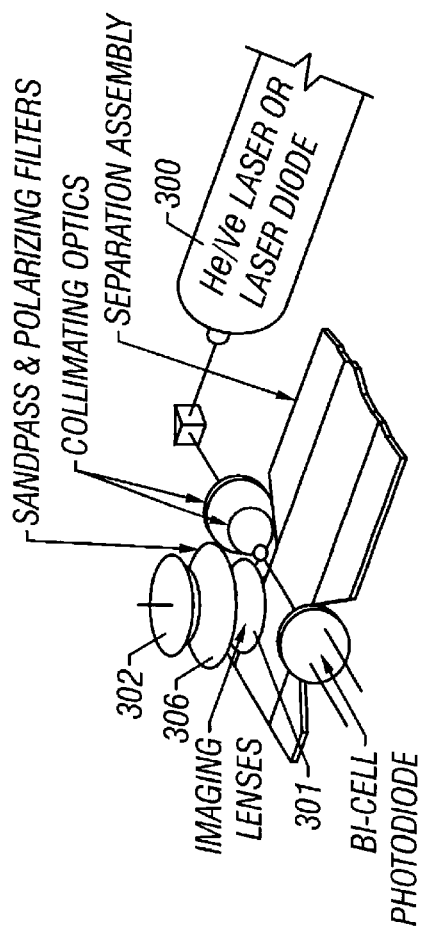
FIG. 3 shows details of the optics of the system.

A specific embodiment of the device is shown in FIGS. 2 and 3. In FIG. 2, the separation assembly is shown in further detail. A channel 200 is coupled to an aluminum heat sink 205. The aluminum heat sink can provide a thermally controlled and uniform environment over the length of the channel.

FIG. 3 shows the fluorescence assembly including a laser diode 300 which can be an He/Ne laser, used in conjunction with available fluorescent labeling chemistry. The laser diode is used with a photo-multiplying tube 215 connected to imaging optics and scanning hardware.

The separation assembly 100 includes the separation matrix itself, and the support structure for the separation matrix. The support structure can be formed of sheet-like plastic material such as DuPont Mylar(™) brand (polyethylene terephthalate), polyester, or DuPont Kapton (™). These materials can be made very thin while still keeping their structural integrity. For example, glass which is thinner then ⅛ inch in thickness would usually require a separate support structure. Sheet plastics such as Mylar and Kapton can be made much thinner then ⅛ inch in thickness without requiring a separate support structure. Since these materials can be made much thinner, the effective thermal conductivity of these materials can be less than would be possible with a glass material. For example, it may be possible to make a device of sheet plastic which has ¹⁄₂₀ the thermal resistance of the similar device made of glass.

Figure 4:
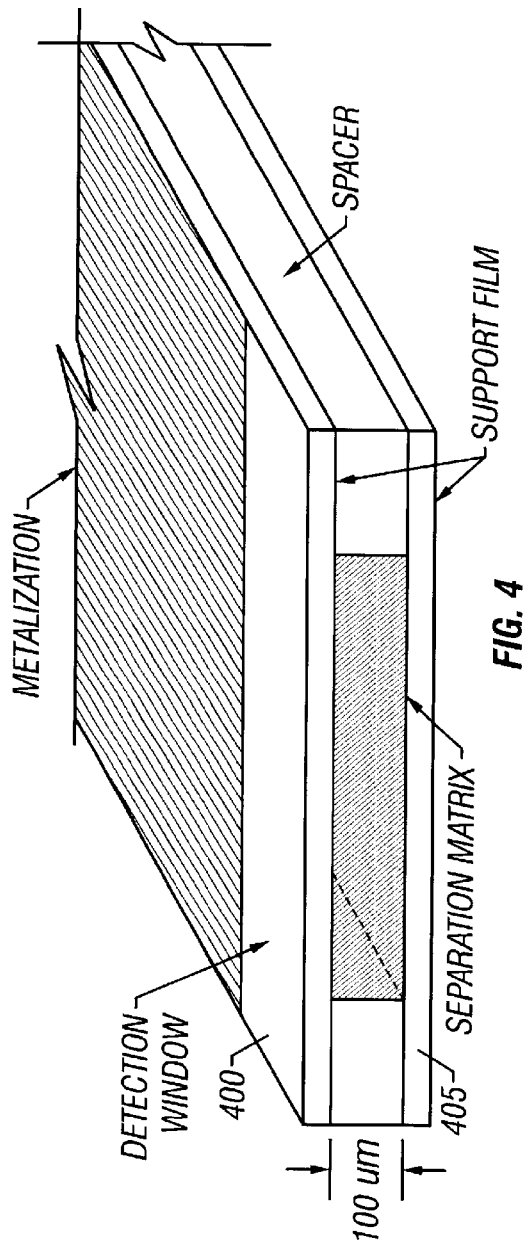
FIG. 4 shows a cross-section of the support assembly.

FIG. 4 shows a hypothetical cross-section along the support structure. Strips of plastic are bonded to form a rectangular tube. The rectangular tube has a cross-section of approximately 10 mm by 0.1 mm. While other cross-sectional dimensions are possible, these dimensions may prove the most practical. The top sheet 400 forms a detection window, and may therefore include an optically transmit said plastic such as polyester or Mylar. The bottom sheet 405 may also be optically transparent. The transparent window may be over the entire assembly, or only near one end of the assembly for the detection region.

The rectangular tube may be filled with a matrix of nucleic acid sequencing gel. This sequencing gel can be, for example, polyacrylamide. Other separation materials can alternately be used, such as agarose, Hydrolink, Longranger, or other aerogels. As known in the art, the gel may be heated to a temperature that denatures the DNA. Then, the gel acts as a sieve to separate the different parts of the DNA based on their molecular weight.

Because the support structure may be constructed of flexible materials, it can be arranged into variety of different forms.

Figure 5A:
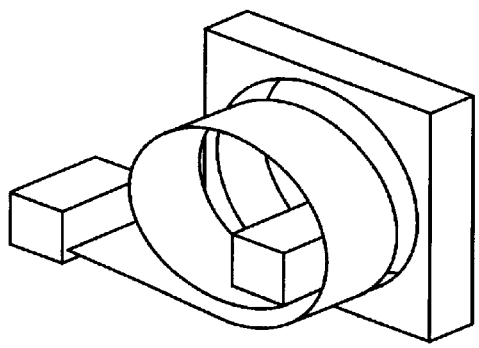
FIGS. 5A–5C show a coiled type instrument.
Figure 5B:
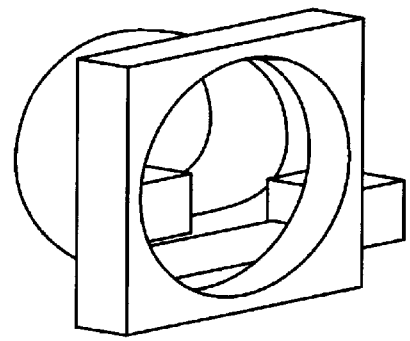
Figure 5C:
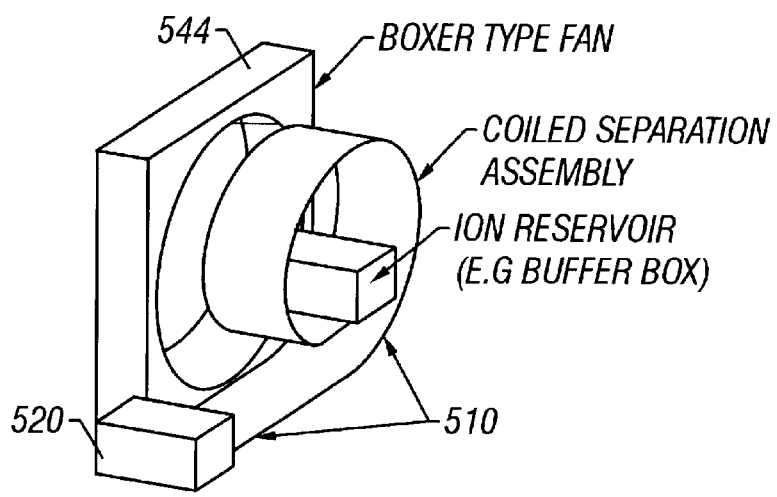
Figure 6:
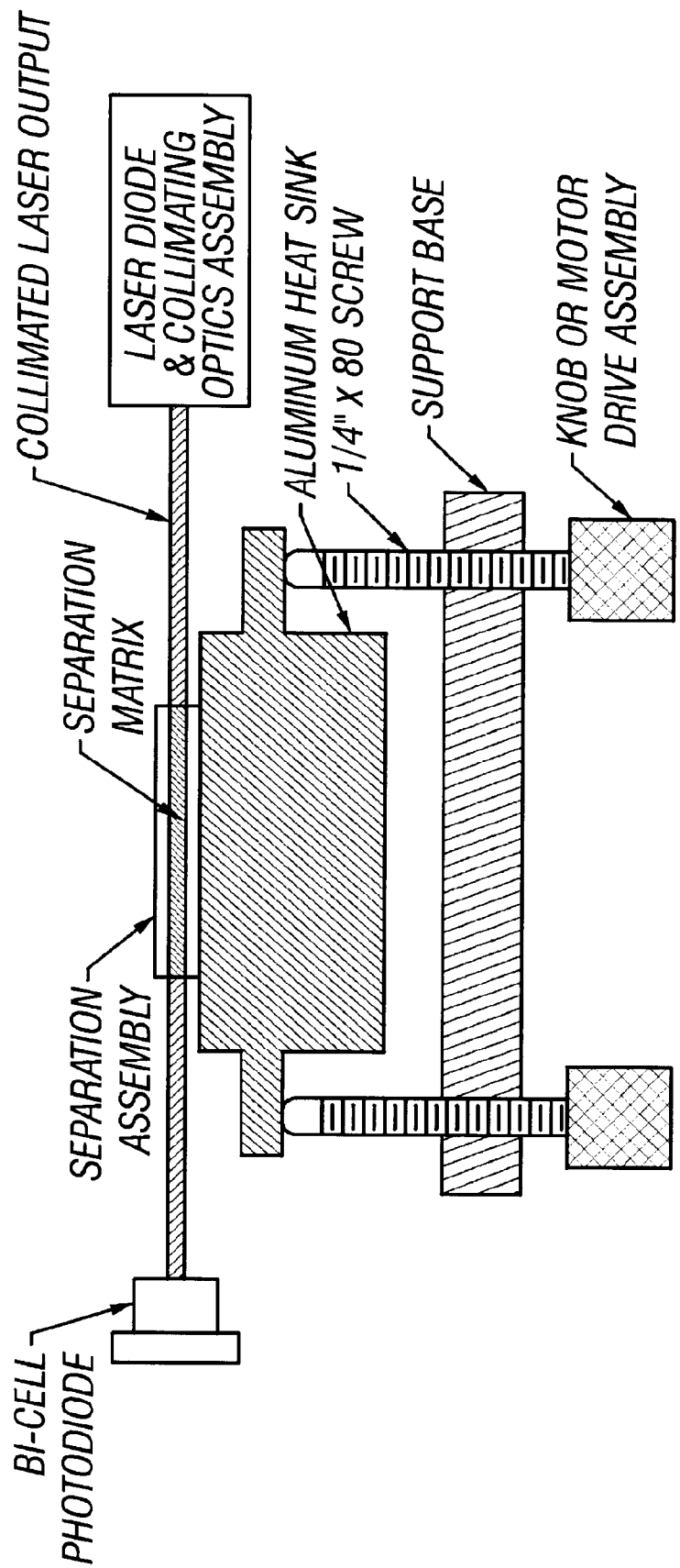
FIG. 6 shows a cross-section of the optical alignment mechanism of the system.

One of the forms may be for example a coiled structure. A coil is shown in FIGS. 5A–5C. The coiled plastic matrix support may form significant advantages. This geometry may enable a more compact and inexpensive instrument. However, the thermal dissipation requirements of such a device may be limited. The separation assembly 500 is coiled as shown in FIG. 5C, and the ion reservoirs 510 and 520 are formed at the two ends of the coil. An extruded separation matrix may also be used.

As shown in the Figure, a fan 544 may be placed near the coil to cool the coil all-at-once, that is to cool the whole length of the coil evenly and avoid thermal gradients.

The width of the matrix may be limited by several factors including Young's modulus for the support material, the support mechanism, dimensional stability requirements for the matrix cross-section, and some optical constraints. However, the width should not be made sufficiently small as to preclude applications of samples that have four individual lanes, one for each base type. These four lanes can use a single label per separation assembly, for example. The assembly can alternately be filled and cured under pressure using a suitable apparatus By using the specified materials described herein, e.g., sheet plastic materials, specifically Kapton and/or Mylar, the assembly could be inexpensive and disposable. This can be supplied as a consumable to the end-user. Otherwise, the user might need to cast acrylamide matrices. This process is not only time-consuming, but also may lead to poor gel to gel reproducability. This may also be dangerous because it may require the use of monomeric acrylamide. This may form a cumulative neurotoxin.

In FIG. 2, in the support assembly is a plastic support assembly resting on an alumina $Al_2O_3$ ceramic insulator. This is attached using thermally conductive epoxy to aluminum heat sink 205. Additional cooling can be provided by one or more boxer-type fans shown generically as 211. These can be placed on one or both sides of the heat sink to provide crossflow cooling. Preferably the airflow is restricted from the top of the structure where the gel assembly is placed in order to avoid formation of thermal gradients.

Aqueous buffer boxes which serve as the ion reservoirs 105 and 100 are placed at each end of the matrix assembly. Each buffer box may include a platinum wire electrode and other conventional ion producing elements. The sample loading can use conventional loading methods is such as a "sharks tooth" comb. However, other sample loading techniques could alternatively be used. With one example is a stacking gel that could be incorporated into one end of the matrix. Another loading system could use the dialysis membrane or glass micro capillary array. Both of the snacking techniques can be used in combination with a DNA absorption step in order to concentrate the DNA samples.

A linear array of microcapillaries can also be used. These microcapillaries are approximately 2 to 3 cm in length with a 100 μm inner diameter and a 400 μm outer diameter. It is noted that using this size will support approximately 20 sample loading spots within the previously described matrix section.

Acid etched silica can be used, for example, as the glass composition. This can facilitate DNA absorption. A porous glass "frit" can be used at the distal end of the loading device. This will allow only small charge carrying ions to traverse the tube. An appropriate voltage gradient can be applied to the tube. DNA is introduced into the tube. Subsequently, the gradient-is reversed to cause the DNA to be injected into the sieving matrix. The DNA in the capillary may be introduced into the gel matrix in this way. The capillaries than function as the wells of the matrix normally formed by combs in more conventional apparatus.

As described, four parallel lanes can be used in such a system. This system can also use sequencing which limits the absolute length of the generated fragments to a range which is best resolved by the instrument. Of course, it may be advantageous to have more lanes, so that more operations to be run in parallel.

As described above, the system can also use materials to eliminate addition of non informational DNA to the separation material.

A plastic plate may be affixed to the top of the system, pressing down on the separation assembly, in order to decrease thermal resistance between the support materials and the heat sink. Thermal grease can also be used to improve the contact. However, thermal grease may cause an associated mess, and therefore may be undesirable in this system. Another purpose of the structural design is to create an isothermal environment for the separation matrix while extracting DNA information, as generated by the applied power.

Metallization can also be applied to the exterior surfaces of the support. The metallization also may improve the heat dissipation and improve temperature uniformity across the separation assembly. If the coiled arrangement of FIG. 5 is used, then the metallization forms a built-in heat sink. Alternatively, a dedicated heat sink could be used with the coiled arrangement. The metallization can be connected to the heat sink assembly to improve heat transfer to the heat sink assembly.

Further production of the isothermal environment can include a constant temperature bath that uses a working fluid such as air or thermally conductive oil.

As conventional, electrophoresis is accomplished by applying a high-voltage, e.g. a voltage greater than 10 Kv. across the length of the matrix using the power supply 120.

Laser Diode fluorescence Excitation is used according to this system. Fluors having excitation (absorption) maximum in the red [630 nm–680 nm] portions of the electromagnetic spectrum have become commercially available. A number of these fluors are based on the cyanine moiety. Commercially available dyes include Cy5, Cy7 and Cy5.5, manufactured by Biological Detection Systems of Pittsburgh, Pa. Other similar materials are available. The Cy5.5 fluor possesses chemical prosthetic groups which makes it easy to label oligonucleotides. These two characteristics, excitation wavelength and the ability to easily incorporate the dye into biological materials, allows Cy5.5 to be used effectively as a fluorescent label for DNA sequence analysis. The other BDS fluors share similar attachment properties, but have shifted excitation/emission wavelengths. Use of these dyes take advantage of the recent advances in shorter wavelength laser diodes, and their inherent cost advantages when compared to any other coherent monochromatic light source. It should be mentions that HeNe sources can also be used to excite these fluors. HeNe sources can also be used to excite these fluors; specifically Cy5. Although not as inexpensive as laser diodes, they are still significantly less expensive than argon ion lasers. Argon ion lasers are currently the most used laser source in biological work, due to the availability and chemical conveniences of fluorescein dye.

Specifically, Cy5.5 labeling is accomplished by reacting the succinylimido-ester of the dye with a derivatized oligonucleotide containing an alkyl amino "spacer". Oligonucleotides containing these spacer groups are readily available commercially. A high pH, aqueous buffer (usually 5 mM borate pH 8.0) for one hour at room temperature is all that is required for the conjugation reaction. As an added benefit, this procedure is far simpler than current DNA fluorescent labeling techniques, such as that employed by the Applied Biosystems kits.

Excitation of the fluorochrome takes place through the side of the matrix, e.g, using a single laser diode excitation source and appropriate collimating optics, as shown in FIG. 3. An acrylamide slab of approximately 1 cm×100 $\mu$m in cross-section, is used because 1 cm is the approximate Rayleigh range of a 100 $\mu$m collimated beam, and 100 $\mu$m is the thickest matrix that can be used without active cooling.

These technique also uses a polarized laser light source, whose plane of polarization may be adjusted to minimize light scattering from the gel matrix. Due to the small diameter of the excitation beam and the practical mechanical tolerances of the assembly, a special arrangement can be used to optically align the gel matrix with the excitation beam. Referring to FIGS. 3 and 5, the output of the laser diode impinges upon a photodiode once it passes through the gel matrix. The heat sink assembly can be supported at the detection end of the matrix by two short, high pitch screws (e.g., a ¼"–80) on either side of the heat sink, FIG. 5. The screw nearest the laser diode is adjusted first, to maximize the output of the photodiode. Next, the second screw, the one nearest the photodiode, could be adjusted to bring the gel matrix into alignment with the excitation beam. The two screws could be motorized and the alignment procedure thus automated.

Fluorescent sequencing methods are being pursued because of two obvious advantages over the use of radio-labels. First, fluorescent methods may have fewer health hazards associated with their use (or the subsequent disposal cost and problems). Also, they are readily detected in real time using photometry techniques, thereby increasing the degree of automation in the end instrument.

The initial use of two to four different chromophores/fluorophores arose from the desire to solve the problem of lane-to-lane mobility differences; a severe problem for automated base calling. This phenomenon may be based on or exacerbated by temperature differentials across the gel.

Unfortunately, an additional problem is inherent in 2 to 4 chromophore/fluorophores sequencing. The different dyes appear to cause their own set of mobility problems. Obviously, solving the thermal problem and using a single fluorescent label greatly simplifies experimental design and the associated instrument, and hence the ultimate cost of any sequencing project. Proponents of the four label technique have advanced the argument that the ability to pace 4 separate reactions per lane will increase the total throughput of the instrument. However, when the increase in mechanical and optical complexity is included, the economic pressures may make this difficult.

The detection optics 125 are placed at the opposite end of the separation assembly from the sample loading area. Different optical detection it systems can be used. The specific detection system shown in FIG. 3 may use a linear photodiode array. Alternatively, however, this may use a CCD array. The laser diode excites the area of detection, and the excitation region is imaged. In FIG. 3, the laser induced flourescene is transmitted and focused by two aspheric lenses, 302 and 304 onto a scanning slit shown as 230. These scanning slits may be 200 micron wide slits arranged radially around a spinning wheel 232. A band pass filter 306 is located between the two aspheric lenses. A polarizing filter may also be located between these two lenses. When the light rays are parallel, the optical band pass filter may achieve its best performance.

Optical edge filters formed of Schott optical glass may be used.

FIGS. 2 and 3 show the transmitted light being detected by a photomultiplier device shown as 215. The resultant photocurrent is converted into a voltage and measured by an A/D converter.

The processor can be a processor or microcontroller of any desired type. The microcontroller controls the individual seeking answer unit to collect data and storing in electronic memory or on a specified medium. The external computer retrieves the stated either via the serial length or directly from the media source.

Alternatively, a dedicated small computer such as a PC can be used.

Another technique described herein facilitates detecting the location of the denatured material without optics. DNA is basically a charged particle. Since DNA has a charge and a polarity, a system may be used which has an electrode in the gel. The electrode detects the resistivity and/or charge of the gel media. In this system, the DNA is denatured, and the gel material acts like a sieve to get separation based on molecular weight. The time when the DNA particle arrives represents information about the material being detected. A characteristic of the gel is electrochemically determined. This characteristic can be pH change in the gel, or resistivity change in the gel. More generally, a change in some electrical parameter of the gel is detected that can be detected with electrodes. By detecting the DNA in this way, the optics are avoided.

Although only a few embodiments have been disclosed in detail above, other modifications are possible.

What is claimed is:

1. A DNA sequencing machine, comprising:
   a plurality of materials, defining an internal chamber which is substantially linear, said materials forming at least left and right side walls and top and bottom walls;
   wherein at least one of said walls has a thermal conductivity which is half or less of the thermal conductivity of glass; and
   a metal coating, coupled to an outside of at least one of said walls.

2. A machine as in claim 1, wherein at least one of said walls has a thickness between 50 and 100 microns.

3. A machine as in claim 2, wherein said walls are formed of one of Kapton™ or Mylar™.

4. A machine as in claim 1, wherein at least one of said walls is formed of a transparent material.

5. A machine as in claim 1, wherein at least two of said walls are formed of sheet plastic.

6. A machine as in claim 1, further comprising a heat sink, coupled to at least one of said walls, and configured to remove heat from said at least one of said walls.

7. A machine as in claim 6, further comprising a high-voltage power supply, establishing a voltage which is effective to allow DNA to be sequenced.

8. A machine as in claim 1, wherein said internal chamber is substantially coiled.

9. A machine as in claim 8, further comprising a fan, configured to blow across an outside surface of said materials, which outside surface is in a coiled shape.

10. A machine as in claim 1, further comprising at least one fan, blowing across an outside surface of said materials.

11. A DNA sequencing machine, comprising:
   a plurality of materials, defining an internal chamber which is substantially linear, said materials forming at least left and right side-walls and top and-bottom walls;
   wherein at least one of said walls has a thermal conductivity which is half or less of the thermal conductivity of glass;
   a heat sink, coupled to at least one of said walls, and configured to remote heat from said at least one of said walls; and
   a metal coating coupled to an outside of at least one of said walls and also to said heat sink.

12. A DNA sequencing machine, comprising:
   a plurality of materials, defining an internal chamber which is substantially coiled, said materials forming at least left and right side walls and top and bottom walls;
   wherein at least one of said walls has a thermal conductivity which is half or less of the thermal conductivity of glass; and
   a metal coating, coupled to an outside of at least one of said walls.

13. A DNA sequencing device, comprising:
   a plurality of walls, defining an internal chamber and an external surface, said plurality of walls each formed of a plastic substance and forming a flexible support structure which allows flexing said internal chamber and external surface;
   a conductive and sieveing gel, filling said internal chamber; and
   a power supply, applying a high voltage between first and second ends of said internal chamber through said gel.

14. A device as in claim 13, wherein said internal chamber is linear in shape.

15. A device as in claim 13, wherein said internal chamber is coiled in shape.

16. A device as in claim 13, further comprising a metallization, coupled to said external surface.

17. A device as in claim 13, further comprising a heat sink, coupled to said external surface.

18. A device as in claim 13, further comprising a preheating element.

* * * * *